United States Patent
Rosengaus

(10) Patent No.: US 7,324,198 B2
(45) Date of Patent: *Jan. 29, 2008

(54) EDGE BEAD REMOVAL INSPECTION BY REFLECTOMETRY

(75) Inventor: Eliezer Rosengaus, Palo Alto, CA (US)

(73) Assignee: KLA-Tencor Corporation, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/527,135

(22) Filed: Sep. 26, 2006

(65) Prior Publication Data

US 2007/0019196 A1 Jan. 25, 2007

Related U.S. Application Data

(62) Division of application No. 10/829,727, filed on Apr. 22, 2004, now Pat. No. 7,142,300.

(60) Provisional application No. 60/467,996, filed on May 5, 2003.

(51) Int. Cl.
*G01J 4/00* (2006.01)
(52) U.S. Cl. ...................................... 356/369
(58) Field of Classification Search ............... None
See application file for complete search history.

(56) References Cited

U.S. PATENT DOCUMENTS 7,142,300 B2 * 11/2006 Rosengaus ............. 356/369

* cited by examiner

*Primary Examiner*—Tu T Nguyen
(74) *Attorney, Agent, or Firm*—Deborah Wenocur

(57) ABSTRACT

A method and apparatus for enhancing image contrast between resist-covered and bare silicon regions of a wafer, applicable to Edge Bead Removal inspection. The wafer is illuminated separately by s-polarized light and p-polarized light impinging at near the Brewster angle of silicon or resist, and an image difference between the reflected s-polarized light and the reflected p-polarized light is derived.

20 Claims, 5 Drawing Sheets

EDGE BEAD REMOVAL INSPECTION BY REFLECTOMETRY

CROSS-REFERENCE TO RELATED APPLICATION

This application is a divisional of U.S. Pat. application Ser. No. 10/829,727 by Eliezer Rosengaus, filed Apr. 22, 2004, now U.S. Pat. No. 7,142,300, and claims priority therefrom. The specification of application Ser. No. 10/829,727 is hereby incorporated by reference in its entirety.

This application is further related to U.S. Provisional Application No. 60/467,996 filed May 5, 2003, and claims priority therefrom.

FIELD OF THE INVENTION

This invention relates to integrated circuit wafer inspection tools, and in particular to a method and apparatus for inspecting a wafer for removal of an edge bead of resist.

BACKGROUND OF THE INVENTION

During the manufacturing process for integrated circuits, lithography (which may include photolithography, e-beam lithography, or X-ray lithography) is generally utilized multiple times as part of patterning steps. The standard method of applying the resist used for lithography is a spin-on method, whereby resist is applied at or near the center of a rotating wafer, causing the resist to spread outwards across the wafer.

The fluid dynamics of spin-coating result in the formation of an "edge bead" of resist, which is located at the wafer edge and is several times as thick as the deposited layer. This edge bead can cause significant problems later in the process if not removed, including flaking which becomes a particulate and contaminant source. Edge beads which are not removed prior to resist development can remain even after a conventional wafer stripping process. It has therefore become standard procedure to remove the edge bead immediately after spin-coating the wafer with resist. This may be accomplished in several ways, including dispensing solvent at the wafer edge and/or optical resist exposure prior to resist development. The removal of the edge bead, if done correctly, leaves a clear annulus of bare silicon at the edge of the wafer. FIG. 1a illustrates an idealized EBR geometry, including prior step stack 2 on wafer 4, resist 6 covering the top 8 and edge 10 of stack 2, and bare silicon region 12 (annular in shape) on the outside edge of wafer 4. Actual resist profiles may be gradual rather than abrupt as shown in the figure. The EBR annulus is generally between 1 and 5 mm in width, and should be accurately centered on the wafer.

One desired feature in optical inspection tools is the ability to do edge-bead removal (EBR) inspection. This includes detection of the position of the ring to determine its position and centering on the wafer, as well as determining if resist removal is complete.

Visual inspection of EBR relies on a color change at the resist edge. However, this method is inaccurate due to the differing absorption spectra and color appearances of various resists. In addition, thin film and diffraction effects may alter the color appearance. Further, if the resist does not have a sharp edge, the optical diffraction effects will be weakened.

Currently used methods for edge bead removal inspection in such inspection systems as the Viper system from KLA-Tencor Corp. utilize integrated reflectance spectra from unpolarized light to locate the edge ring where the resist has been removed. This method has proven to work well for the first resist layer. However, as illustrated in FIG. 1b, actual edge profiles for multilayer structures can be considerably more complex than the idealized profile shown in FIG. 1a. Slight differences in the centering or width of the resist region cleared at each step can result in a stepped profile 16 with multiple rings 18 of varying heights and materials underlying the resist. This complicates the optical reflectance results and causes further inaccuracies in inspection.

SUMMARY OF THE INVENTION

It is therefore an object of this invention to provide an improved integrated circuit manufacturing method and apparatus for edge bead removal inspection.

It is a further object of this invention to provide an improved integrated circuit manufacturing method and apparatus for edge bead removal inspection which is accurate for multilayer structures.

It is a further object of this invention to provide an integrated circuit manufacturing method and apparatus for edge bead removal inspection which is low cost and compatible with existing inspection systems.

DETAILED DESCRIPTION OF THE INVENTION

My inventive method and apparatus provides an increased contrast between resist-covered regions of the wafer and regions without resist, in particular bare silicon regions. This increased contrast improves resolution near the wafer edge, which is inherently a noisy area in terms of reflectance measurements. The inventive method differs from standard ellipsometry, which generally utilizes a point light source, varying wavelengths and polarizations at a single spot. Using ellipsometry, material layers, thicknesses, and indices of refraction can be determined locally.

In contrast, the present invention is an imaging method which increases contrast over an extended area. The light source is required to be collimated, but may be extended rather than being a point source; e.g, it may be a spot or a line source.

Figure 1A:
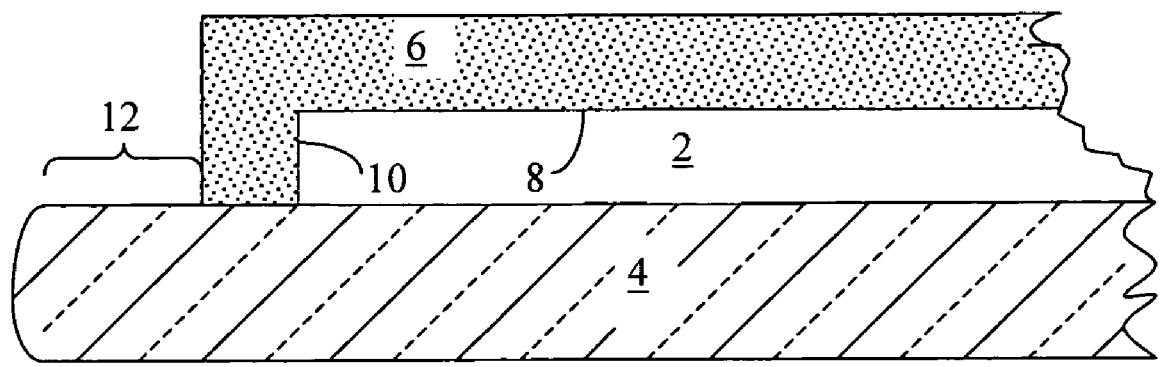
FIG. 1a is an illustration of an idealized Edge Bead Removal geometry.
Figure 1B:
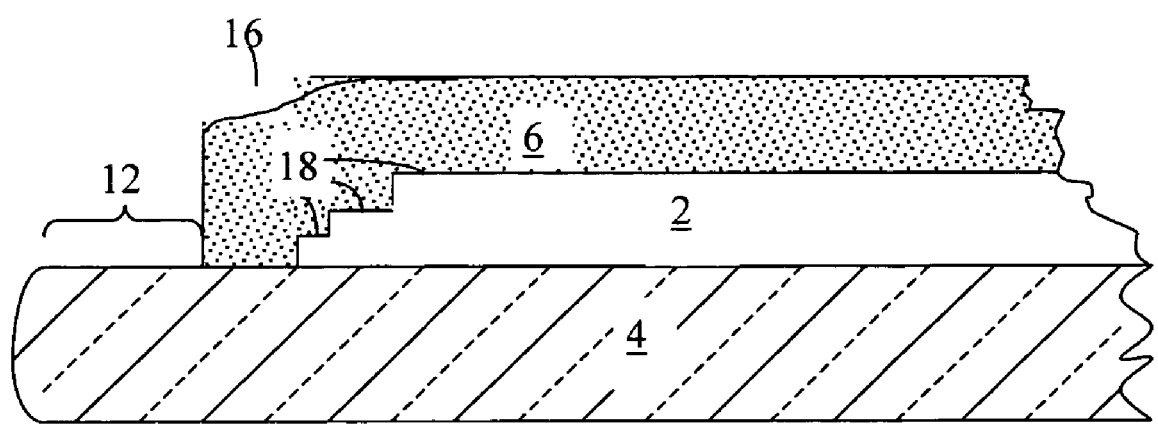
FIG. 1b is an illustration of a realistic profile for Edge Bead Removal.
Figure 2:
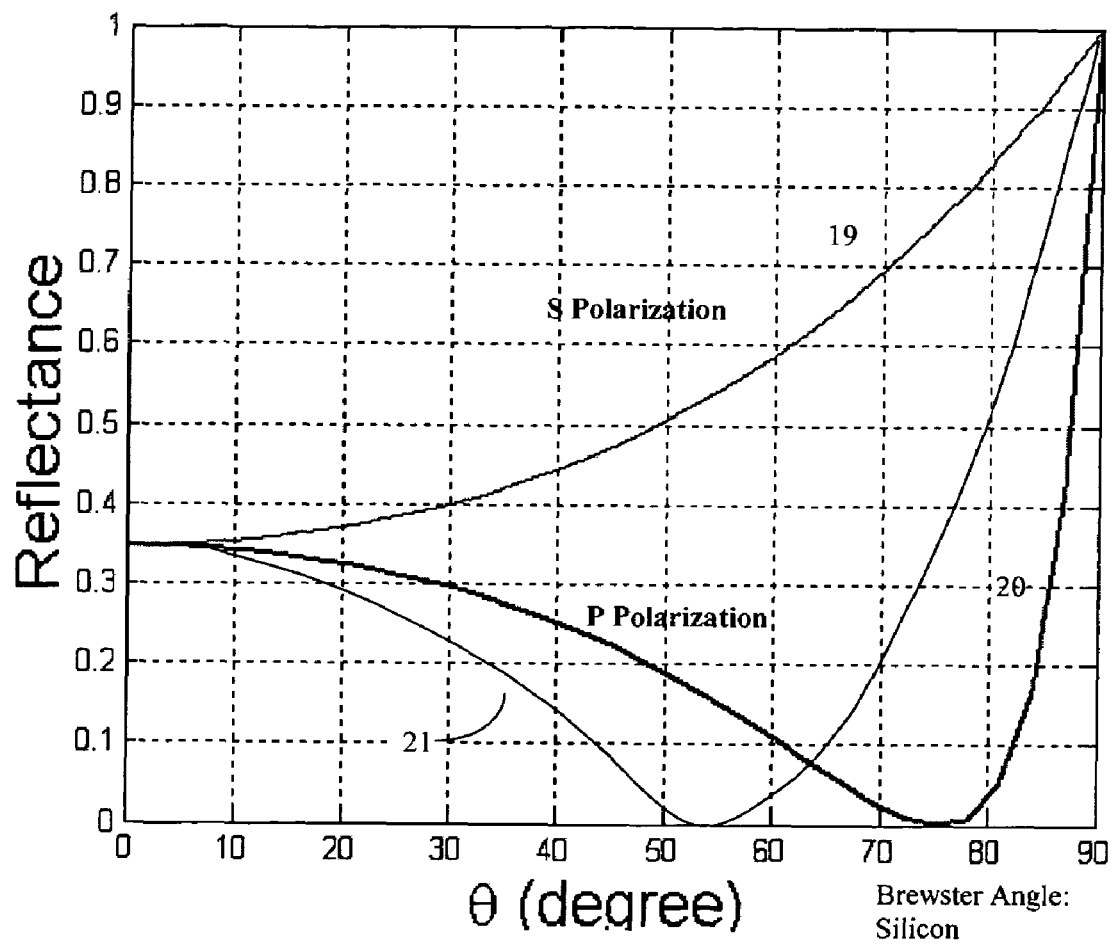
FIG. 2 is a graph of reflectance coefficients as a function of angle of illumination from normal, for silicon.

FIG. 2 illustrates the generic behavior expected for reflected light from a material (i.e., a silicon wafer) when the illuminating, i.e., incident light, is collimated and linearly polarized. The figure is a graph of the reflection coefficients from silicon as a function of angle of illumination from normal, for s-polarized and p-polarized incident light. Wavelength for this data is 635 nm. P-polarized light has an electric field vector in the plane of incidence defined by the propagation vector of the incident plane wave and the normal vector to the surface. The electric field for p-polarized light therefore has a component normal to the surface.

S-polarized light has an electric field vector perpendicular to the plane of incidence, therefore its electric field is tangential to the surface and has no normal component.

As shown in FIG. 2, the reflectivity curve 19 for s-polarized light from silicon increases monotonically as the angle of illumination increases from the normal. This curve is qualitatively similar to the reflectivity curve for s-polarized light from most materials for flat sample surfaces: the numerical values depend on the index of refraction. However, the reflectivity curve 20 for p-polarized light decreases to zero at an angle known as the Brewster angle, which is approximately 77 degrees for silicon. The Brewster angle is determined (for illumination through air of a material having index of refraction n) according to the equation $$\tan \theta_{Brewster} = n$$

Reflection coefficient curves from materials other than silicon will resemble those in FIG. 2 qualitatively, but having different values for the Brewster angle and thus different ratios of reflectivity between s-polarized and p-polarized light at various angles. Variations will be the greatest between materials having greatly differing indices of refraction.

Silicon, having n=4.6, has a Brewster angle of approximately 77 degrees from normal. In contrast, resist typically has n approximately 1.5, resulting in a Brewster angle of approximately 56 degrees from normal. An illustrative approximate reflectivity curve 21 for p-polarized light from resist is shown as a dotted line in FIG. 2.

According to my inventive concept, a wafer is illuminated at the Brewster angle for silicon, and the reflected light image is observed in both s- and p-polarizations. In a first embodiment, the image acquired in p-polarization is subtracted from that acquired in s-polarization, yielding an "image difference". Note that for the bare silicon region, there will be little or no p-polarized reflected light at the silicon Brewster angle, therefore the image difference will be essentially the same as the s-polarized image. In contrast, for the resist-covered region, the p-polarized light will be significantly reflected at the silicon Brewster angle, and the image difference will be significantly less bright than the s-polarized image. Sensitivity is maximized by using the image difference method. In this embodiment, identification of regions can be accomplished by thresholding the image differences, i.e, by assigning the characteristic that less than a certain difference is resist, and greater than a certain difference is bare silicon.

In a second embodiment, image differences are not created, but the p-polarized images are compared in the different regions, for light incident at a Brewster angle. For example, if the angle of incidence of the p-polarized light is the Brewster angle for silicon, the silicon regions will evidence little or no reflectance and will appear dark. In contrast, at that angle, there is significant reflectance from the resist-covered regions, which will appear considerably brighter than the silicon regions. Substantial contrast enhancement is thereby obtained using p-polarized light at the Brewster angle for silicon, as compared with the use of unpolarized light.

Both embodiments of this method therefore provide artificially enhanced image contrast between the bare silicon regions and the resist-covered regions. This enhanced contrast can help overcome the inherent noise present in the image near the wafer edge. It can also improve performance when multiple edge rings are present from earlier process steps.

Alternative embodiments of the method utilize illumination angles other than the Brewster angle for silicon. The contrast enhancement will be greatest, however, at illumination angles close to either the silicon Brewster angle or the resist Brewster angle.

Figure 3:
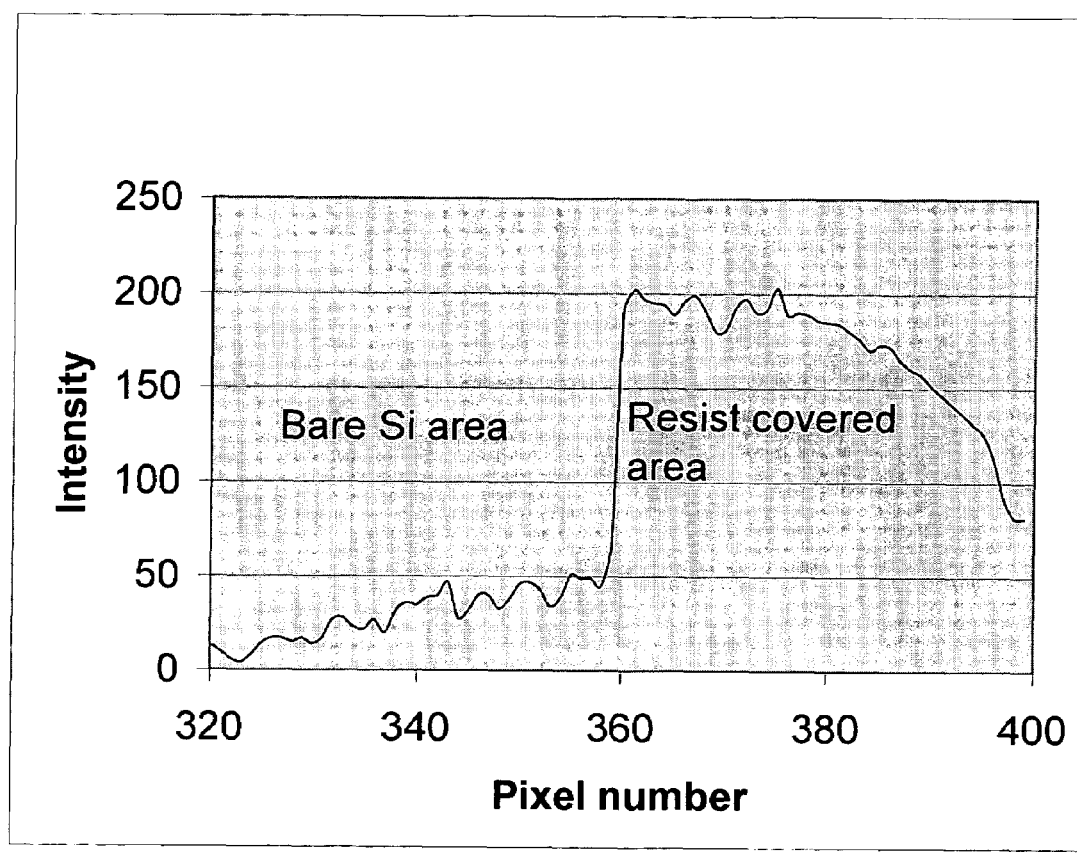
FIG. 3 is a graph of reflected light intensity across a silicon/resist boundary using the inventive method.

FIG. 3 is a graph of an experimental intensity profile of reflected light across a silicon/resist transition, using collimated illumination (incandescent filtered light) at the silicon Brewster angle. It is seen that an extremely sharp transition in reflectance occurs at the silicon/resist boundary, yielding enhanced image contrast.

Figure 4:
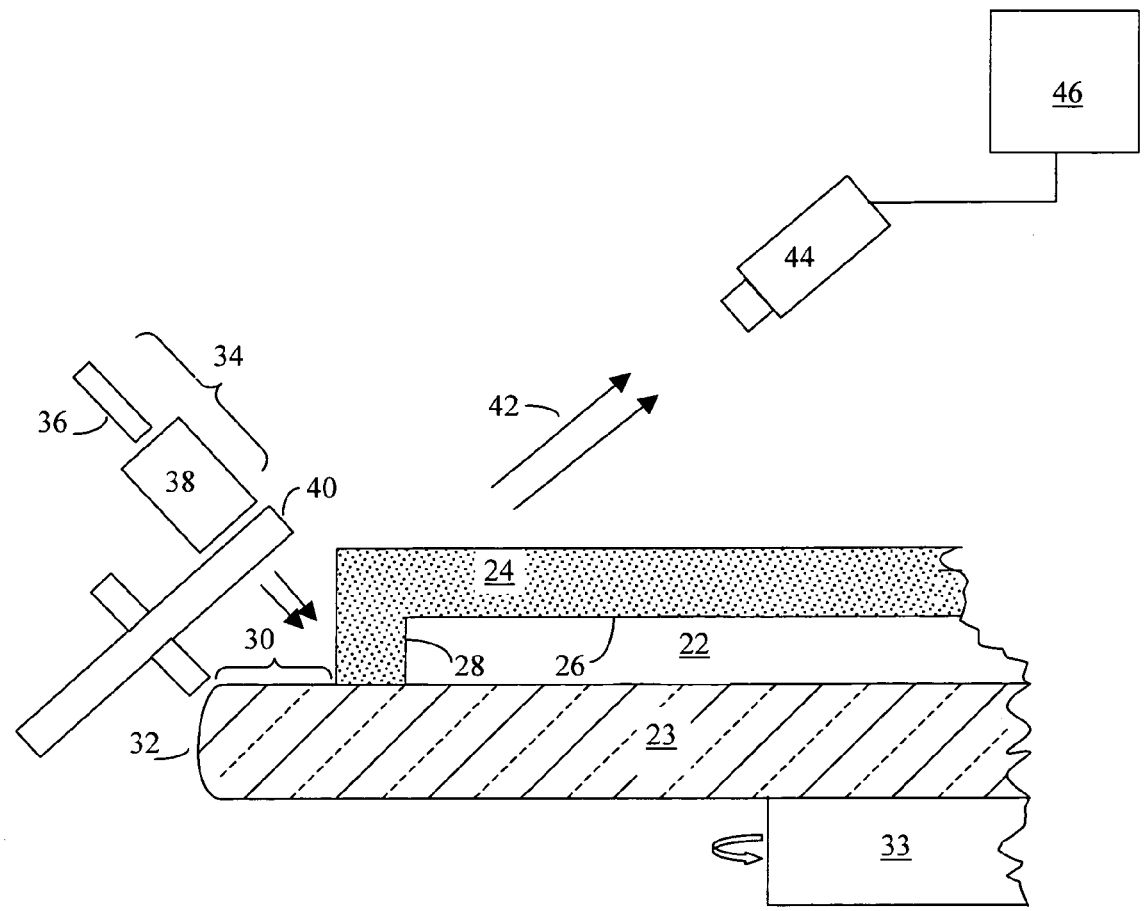
FIG. 4 is an illustration of an apparatus suitable for implementing the inventive method.

An embodiment of an apparatus suitable for implementing the inventive method is shown in FIG. 4.

Silicon wafer 23 has prior step stack 22 thereon, and atop prior step stack 22 is patterned resist layer 24, which ideally completely covers top surface 26 and side surface 28 of prior step stack 22. Edge Bead Removal (EBR) annulus 30 near edge 32 of wafer 23 is ideally completely stripped of resist, with only bare silicon remaining. Silicon wafer 23 is mounted on rotating pre-aligner 33. Illumination source 34 may be an expanded laser beam produced by sending a beam from laser 36 through beam expander 38, or alternatively it may be a collimated incandescent light source or other collimated, two-dimensional light source. Polarizer 40 may comprise a filter wheel and/or a quarter wave plate.

Reflected light 42 is captured by image detection system 44, which may comprise an imaging lens and a low-resolution CCD or camera. Image processor 46 may comprise a frame grabber, USB interface, or Firewire interface leading into a computer. Analog imaging may also be done. Using standard components, image resolution is expected to be on the order of 40 micron pixel size.

The aforementioned apparatus can be easily incorporated into a more complete edge inspection apparatus which inspects for criterion in addition to Edge Bead Removal. For example, edge chipping, caused by wafer handling by equipment, is of concern. A chipped wafer has a high probability of shattering in such later processing steps as anneal or deposition, which can contaminate a chamber or a whole lot of wafers. Another edge effect which is of concern is the presence of chips, defects, or unwanted deposits such as resist on the backside edge of the wafer.

An inclusive edge inspection module could combine the apparatus described above for the EBR, and could also incorporate illumination from another angle to inspect for edge chips. Due to their irregular shape, chips cause a large amount of scattering, particularly in dark field. The additional illumination could come from a second light source, e.g., a laser or LED, or alternatively could use the same light source used for EBR if the angle of incidence or azimuthal angle could be adjusted. Such an edge inspection system could be mounted on the pre-aligner and use a line camera for detection: In this way the rotation of the pre-aligner chuck would scan the line across the wafer to form the image.

Inspection of the wafer backside could be incorporated into the edge inspection system by displacing the camera or sensor slightly such that some of it looks at the topside edge area of the wafer for EBR and edge chips, but that some of it views the area slightly off the wafer. A mirror could then be positioned such that the sensor portion off the wafer would collect reflected light off the back of the wafer to look for chips, defects, or deposits on the back edge of the wafer.

The edge inspection module as described above could be implemented into a standard inspection system at minimal cost: the only additions would be a small camera and a light source.

My inventive concept of utilizing differential reflectance from s- and p-polarized incident light from an extended collimated light source to enhance image contrast between silicon and resist-covered regions can be implemented inexpensively with standard components as described above. The necessary apparatus could be manufactured separately and retrofitted into existing equipment or produced as OEM (Original Equipment Manufacturer).

Using my invention, image contrast between resist-covered regions and bare silicon regions is greatly enhanced. This allows for more effective Edge Bead Removal inspection, especially at later stages when multiple layers have been patterned. The same method and apparatus could be used at other regions on the wafer for such applications as inspecting for complete development and removal of resist after exposure, or inspecting for complete etch or polish during processing. Another possible use is to detect holes or voids in layers such as spin-on layers. The necessary criterion to allow for the use of my inventive method for the aforementioned applications is that the indices of refraction of the two materials in question be quite different from each other in order to enable the image enhancement.

The invention is not intended to be restricted to the exact embodiments described above. It should be apparent to those skilled in the art that modifications can be made without departing from the inventive concept. For example, other image detection devices could be utilized, and collimated light sources other that expanded lasers or collimated incandescent light could be used, such as shaped fiber optic bundles. The scope of the invention should be construed in view of the claims.

I claim:

1. A method of enhancing image contrast between a first material and a second material on a sample surface, said sample surface being comprised of a first portion having said first material exposed thereon and a second portion having said second material exposed thereon, said first and second materials having substantially different indices of refraction, comprising the steps of:
    a) providing a collimated illumination beam directed toward said sample surface at an angle of illumination, said collimated illumination beam illuminating an extended area of said sample surface, said angle of illumination being at angle $\theta$ from a normal to said sample surface, said angle $\theta$ being selected such that the ratio of reflectivity between s-polarized light and p-polarized light is substantially different for said first material as compared to said second material at an angle of illumination equal to said angle $\theta$;
    b) polarizing said collimated illumination beam so as to yield a p-polarized portion of said collimated illumination beam impinging on said sample surface;
    c) detecting an extended-area image of reflected light from said p-polarized portion of said collimated illumination beam off of said sample surface; and
    f) processing said image of reflected light from said p-polarized portion of said collimated illumination beam to enhance said image contrast between said first material and said second material over said extended area.

2. The method of claim 1, further comprising the steps of: before or after steps b) and c),
    d) polarizing said collimated illumination beam so as to yield an s-polarized portion of said collimated illumination beam impinging on said sample surface;
    e) detecting an extended area image of reflected light from said s-polarized portion of said collimated illumination beam off of said sample surface; and wherein
said step f) of processing said image of reflected light from said p-polarized portion of said collimated illumination beam to enhance said image contrast between said first material and said second material further includes processing said image of reflected light from said s-polarized portion of said collimated illumination beam.

3. The method of claim 2, wherein said angle $\theta$ is selected to be approximately equal to the Brewster angle of one of said first and said second material.

4. The method of claim 2, wherein said first material is silicon and said second material is resist.

5. The method of claim 2, wherein said collimated illumination beam is an extended two-dimensional beam.

6. The method of claim 5, wherein said collimated illumination beam is an expanded laser beam.

7. The method of claim 5, wherein said collimated illumination beam is a collimated incandescent beam.

8. The method of claim 2, wherein said steps b) and d) comprise passing said collimated illumination beam through a filter wheel.

9. The method of claim 2, wherein said steps b) and d) comprise passing said collimated illumination beam through a quarter wave plate.

10. The method of claim 2, wherein said steps c) and e) comprise capturing said reflected light from said s-polarized portion of said collimated illumination beam and from said p-polarized portion of said collimated illumination beam with an imaging lens and a camera.

11. The method of claim 2, wherein said step of processing said image of reflected light from said s-polarized portion of said collimated illumination beam and said image of reflected light from said p-polarized portion of said collimated illumination beam to enhance said image contrast between said first material and said second material comprises forming an image difference between said image of reflected light from said s-polarized portion of said collimated illumination beam off of said sample surface and said image of reflected light from said p-polarized portion of said collimated illumination beam off of said sample surface.

12. An apparatus for enhancing image contrast between a first material and a second material on a surface of a sample, said sample surface being comprised of a first portion having said first material exposed thereon and a second portion having said second material exposed thereon, said first and second materials having substantially different indices of refraction, comprising:
    a) an illumination source for providing a collimated two dimensional illumination beam, said collimated two dimensional illumination beam illuminating an extended area of said sample surface, to impinge, at an angle of illumination, on said sample surface held in the path of said illumination beam, said angle of illumination being at angle $\theta$ from a normal to said sample surface;
    b) a polarizer positioned between said illumination source and said sample surface and in the path of said illumination beam, said polarizer being adjustable so as to choose between transmission of s-polarized light and p-polarized light;
    c) an image detection system for detecting an extended area image of reflected light from said collimated illumination beam off of said sample surface; and d) an image processor coupled to said image detection system, for processing said image of reflected light from said collimated illumination beam to enhance said image contrast between said first material and said second material.

13. The apparatus of claim 12, wherein said image processor is configured to form an image difference between an image of reflected light from an s-polarized portion of said collimated illumination beam off of said sample surface and an image of reflected light from a p-polarized portion of said collimated illumination beam off of said sample surface.

14. The apparatus of claim 12, wherein said illumination source comprises a laser and a beam expander.

15. The apparatus of claim 12, wherein said illumination source comprises an incandescent light and a collimator.

16. The apparatus of claim 12, wherein said illumination source is adjustable in angle of illumination.

17. The apparatus of claim 12, wherein said polarizer comprises a filter wheel.

18. The apparatus of claim 12, wherein said polarizer comprises a quarter wave plate.

19. The apparatus of claim 12, wherein said image detector comprises an imaging lens and a camera.

20. The apparatus of claim 12, wherein said image processor comprises a computer coupled to said image detector.

* * * * *